United States Patent [19]

Craig et al.

[11] Patent Number: Plant 7,538

[45] Date of Patent: May 28, 1991

[54] REGAL PELARGONIUM NAMED 'FANTASY'

[75] Inventors: Richard Craig; Leon Glicenstein, both of State College, Pa.

[73] Assignee: Research Corporation Technologies, Inc., Tucson, Ariz.

[21] Appl. No.: 370,502

[22] Filed: Jun. 22, 1989

[51] Int. Cl.[5] ..... A01H 5/00
[52] U.S. Cl. ..... Plt./68
[58] Field of Search ..... Plt./68

[56] References Cited

U.S. PATENT DOCUMENTS

P.P. 6,072 12/1987 Kirmann ..... Plt. 68

*Primary Examiner*—James R. Feyrer
*Attorney, Agent, or Firm*—Scully, Scott, Murphy & Presser

[57] ABSTRACT

This invention relates to a new and distinct cultivar of regal pelargonium (*Pelargonium* ×*domesticum*) named 'Fantasy' substantially as illustrated and described herein, particularly characterized as being compact and self-branching, early flowering and floriferous, and having a maroon blotch fading to a blush pink background on the upper petals and lighter blush pink to near white lower petals.

2 Drawing Sheets

BACKGROUND OF THE INVENTION

The present invention relates to a new and distinct cultivar of regal pelargonium (*Pelargonium*×*domesticum*) called 'Fantasy'. The cultivar is characterized as being compact and self-branching (without pinching), early flowering and florifarous. The flowers have a maroon blotch on the upper petals that fades to a blush pink or near white margin in contrast to blush pink to near white lower petals.

The cultivar was developed from an organized, scientifically designed breeding program conducted at the Department of Horticulture, The Pennsylvania State University, University Park, PA 16802. The objective was to produce a new regal Pelargonium gentoype with excellent propagation characteristics, compact growth habit, predictable and consistent flowering response, and acceptable postharvest quality. 'Fantasy' resulted from selection from the progeny of the cross-pollination of regal pelargonium cultivars 'Miss Cherryvale' and 'Virginia'. 'Fantasy' maintained the maroon color of 'Miss Cherryvale' in the upper petals and the two-color flower color and early flowering ability of 'Virginia', a commercial standard. The cultivar flowers a few days later than 'Virginia' in early spring trails and equal to 'Virginia' in late spring trials. The selection was asexually propagated by cuttings and the reproductions ran true.

'Fantasy' is similar to the patented cultivar Lucy in flower part coloration, floriferousness, early flowering ability, and warm temperature flower initiation. In comparison to Lucy, 'Fantasy' has diverse parentage, has a blush pink flower color background as opposed to lilac or lavender, has different leaf numbers and floret confirmation, and is not characterized as vigorous in growth habit.

With reference to the detailed description of the cultivar which follows, the test plant was potted in soilless medium and grown in a greenhouse under natural sunlight, at a night temperature of approximately 58° F. and a day temperature of approximately 68° F. Fertilizer was applied in every watering with 200 ppm nitrogen provided in the forms of 15-16-17 (two consecutive waterings) and 20-0-20 (every third watering) in a repeating cycle.

Color readings were taken under incandescent light at approximately 200 foot candles and color identification was by reference to The Royal Horticultural Society Colour Charts, except where common terms of color definition are employed.

SUMMARY OF THE INVENTION

This invention relates to a new and distinct cultivar of regal Pelargonium (*Pelargonium*×*domesticum*) named 'Fantasy' that is characterized as being compact and self-branching, early flowering and floriferous, and having a maroon blotch fading to a blush pink background on the upper petals and lighter bluch pink to near white lower petals.

DESCRIPTION OF THE PREFERRED EMBODIMENT

The Plant

Figure 1:
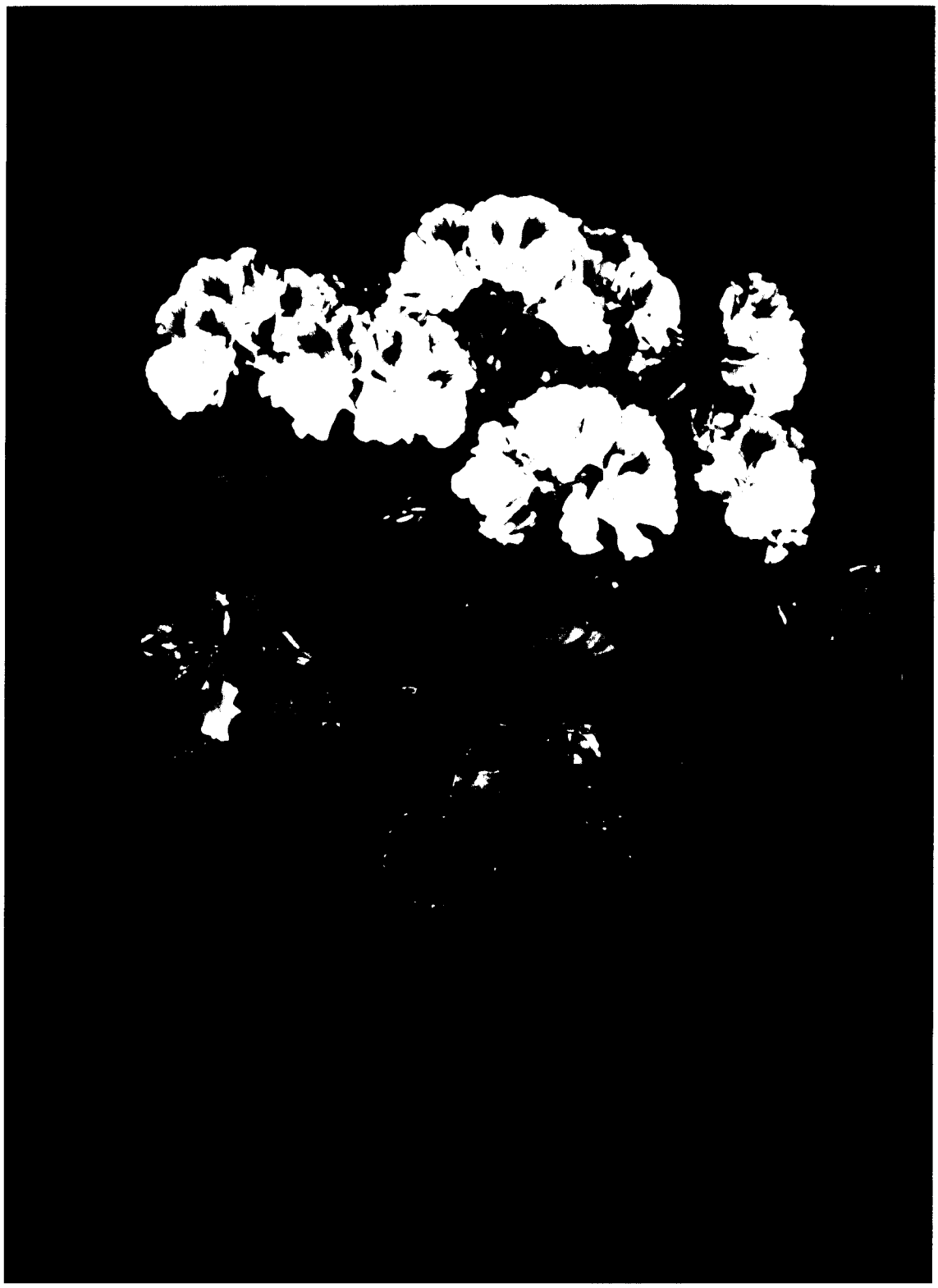
FIG. 1 illustrates in color the cultivar including foliage and flowers.
Figure 2:
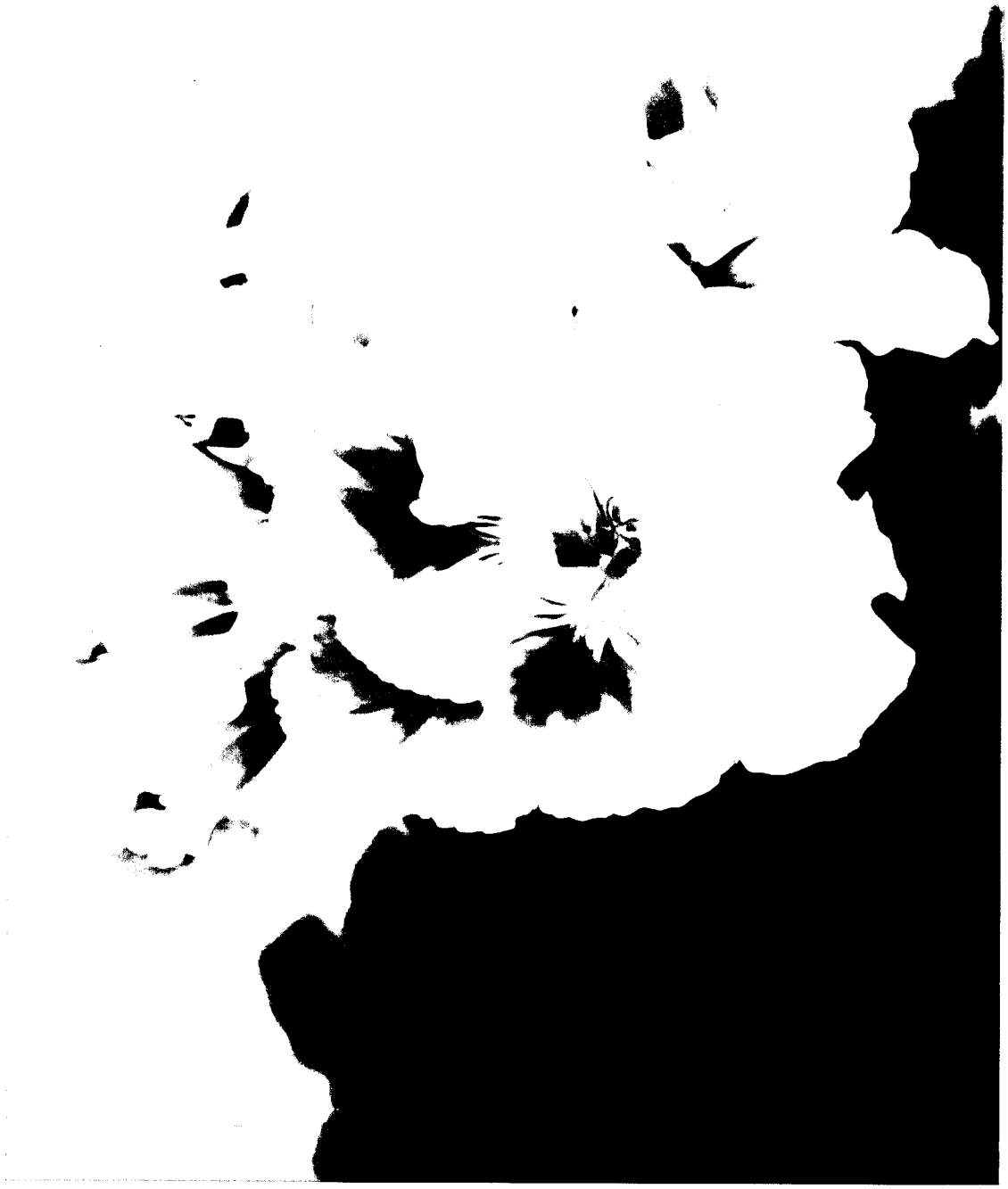
FIG. 2 illustrates in color primarily the floret.

Classification:

*Botanical.*—*Pelargonium*×*domesticum.*

*Tradename.*—#284-(80-26-1).

Form: Compact, self-branching.

Height: 13–21 cm, will vary with environment and cultural conditions.

Growth: Free branching from base; short internodes; stands upright with no artificial support.

Leaves:

*Size.*—Largest measured 7.0 cm long ×12.0 cm wide.

*Shape.*—Depressed ovate; base is cuneate to truncate to reniform; variously lobed; ratio of length to width is 2 to 3.

*Margin.*—Toothed.

*Texture.*—Pubescent.

*Color.*—Adaxial: Green 143C. Abaxial: Green 139D.

*Ribs and veins.*—Palmate venation:

*Petioles.*—Texture: Lightly pubescent. Length: Up to 9.0 cm long. Color: Yellow-green 144B.

Stem:

*Internode length.*—Up to 2.3 cm.

*Color.*—Yellow-green 145A.

The Flower

Blooming habit: Average earliness, 11 weeks to flower; floriferous.

Inflorescence form: Umbellate.

Inflorescence size: Varies with floret number; often 8.0–10.0 cm across (with florets fully open).

Inflorescence number: 11–13 inflorescenses at first bloom, comparable to 'Virginia'.

Inflorescence position: Inflorescences rise well above the foliage.

Disease resistance: Not known.

Florets:

*Number.*—Up to 10 per inflorescence (most were 5–8).

*Forms.*—Cupped.

*Size.*—4.0–5.0 cm across open floret.

Petals:

*Number.*—5–7.

*Texture and appearance.*—Smooth, with ruffled margins; undulated surface.

*Color.*—1st Floret to open: Adaxial: All petals red-purple 68D. Abaxial: All petals red-purple 69A. Successive florets: Upper petals: Adaxial: Basal attachment: White with red 53C to 53B veins, some 53A. Central zone and veins: Red-purple 61A or red 53A and fading to red-purple 61C. Feathering in distal portion surrounding central zone: Red 45D or 47B fading to red-purple 62D or red 56D to near white margin. Abaxial: Red 48D. Lower petals: Adaxial: Basal attachment: White to near white, ⅓ to ½ of petal. Distal zone: Red-purple 62D, occasional small blotches red-purple 61C. Veins: Red-purple 62D, occasionally red-purple 61C. Abaxial: Red-purple 62D.

Petaloids:

*Number.*—0, 1, or 2.

*Shape.*—Petal-like (often attached to a sepal).

*Color.*—Similar to the color of the petals.

Sepals:

*Number.*—5–7.

Pedicel: Subtended by bracts.

*Length.*—Up to 3.0 cm.

*Color.*—Yellow-green 144A.

Peduncle: Arises from node; opposed to leaf petiole; subtended by leaves and bracts.

*Length.*—Up to 10.0 cm.

*Color.*—Yellow-green 144A.

Reproductive Organs

Androecium:

*Stamens.*—7–9 flat, ribbon-like filaments, joined at their bases; upper ⅓ of filaments is pale purple; versatile attachment to anthers which are light purple and well developed and introrse; orange pollen.

*Staminodes.*—2–5 flat, ribbon-like filaments with no athers.

*Petaloid stamens.*—None observed.

Gynoecium:

*Pistil number.*—1.

*Length.*—20.0–25.0 mm.

*Stigma.*—5–7 parted; purple.

*Style.*—Up to 10.0 mm long; purple.

*Ovary.*—Up to 7.0 mm long; superior; very pubescent; yellow-green.

Fruit: Schizocarp; rarely observed.

I claim:

1. A new and distinct cultivar of regal Pelargonium substantially as illustrated and described herein, particularly characterized as being compact and self-branching, early flowering and floriferous, and having a maroon blotch fading to a blush pink background on the upper petals and lighter blush pink to near white lower petals.

* * * * *

UNITED STATES PATENT AND TRADEMARK OFFICE

CERTIFICATE OF CORRECTION

PATENT NO. : Plant 7,538

DATED : May 28, 1991

INVENTOR(S) : Richard Craig, et al

It is certified that error appears in the above-identified patent and that said Letters Patent is hereby corrected as shown below:

Column 1, line 7, "florifarous" should read as --floriferous--.

Column 1, line 15, "Pelargonium" should read as --pelargonium--.

Column 2, line 12, "Pelargonium" should read as --pelargonium--.

Column 4, line 25, "athers" should read as --anthers--.

Column 4, line 30, "7 parted" should read as --7-parted--.

Column 4, line 37, "Pelargonium" should read as --pelargonium--.

Signed and Sealed this

Fifth Day of January, 1993

*Attest:*

*Attesting Officer*

DOUGLAS B. COMER

*Acting Commissioner of Patents and Trademarks*